United States Patent [19]

Simpson

[11] Patent Number: 4,655,814

[45] Date of Patent: Apr. 7, 1987

[54] WATERWAYS TREATMENT COMPOSITION AND METHOD

[76] Inventor: Bobby R. Simpson, 10072 Trask, Garden Grove, Calif. 92643

[21] Appl. No.: 742,535

[22] Filed: Jun. 7, 1985

[51] Int. Cl.$^4$ ............... A01N 63/00; C12N 9/00; C07G 17/00; C02F 1/68
[52] U.S. Cl. ...................... 71/67; 435/183; 435/267; 210/764
[58] Field of Search ............. 435/183, 262, 267, 946, 435/257; 71/67; 210/764

[56] References Cited

U.S. PATENT DOCUMENTS 4,042,367  8/1977  Wilson .................... 71/66

OTHER PUBLICATIONS

The C. B. Dolge Co., "New Dolge Lake and Pond Dye", Sep. 1970; fact sheet dated 8/19/71.

Primary Examiner—Lionel M. Shapiro
Attorney, Agent, or Firm—Allen A. Dicke, Jr.

[57] ABSTRACT

The composition and method are for waterways, usually closed cycle, in which algae and the like is to be killed without harm to higher animal life. The composition includes a violet dye to enhance ultraviolet light penetration from the prevailing light to enter the waterway. This ultraviolet light, with reduction in visible light, causes algae death. It also increases free oxygen, neutralizes some toxins, and reduces admission of infrared radiation. The composition includes an enzyme which digests the dead algae and similar material. The products of digestion are such as to leave clean water. A blue dye may optionally be used to hide the violet color of the water in the visible part of the spectrum.

25 Claims, 3 Drawing Figures

WATERWAYS TREATMENT COMPOSITION AND METHOD

BACKGROUND OF THE INVENTION

This invention is directed to a composition including violet dye and a digestive enzyme for the treatment of waterways in order to kill the algae and like materials therein, without toxic effect on higher life.

Closed system waterways are often used as part of landscape planning in business parks and residential apartment or condominium complexes. These waterways often include a pond from which water is pumped to produce a waterfall. Often a flowing stream is provided below the water flow to return the flowing water to the pond. These waterways are subject to growth of algae and other cryptogamia. Overgrowth of such plants can harm the waterway by requiring excessive oxygen to the detriment of other plants and fish and may lead to putrefaction. It is desirable to limit or eliminate such growth in waterways of that nature. While the composition and method of this invention are particularly useful for closed system waterways, they are also useful in natural lakes, ponds and streams for the same purpose.

SUMMARY OF THE INVENTION

In order to aid in the understanding of this invention, it can be stated in essentially summary form that it is directed to a waterways treatment composition and method which includes a violet dye which, when mixed with the water in the waterway to be treated, enhances ultraviolet light penetration to kill cryptogamia in the water, and includes an enzyme to digest the killed cryptogamia. A blue dye is optionally included for hiding the color of the violet dye.

It is, thus, an object and advantage of this invention to provide a waterways treatment composition and method for the controlling of growth of cryptogamia and the like.

It is a further object and advantage to provide such a composition and method which is inexpensive to use, is effective, and is safe to humans and other animal life in the water.

It is a further object and advantage to employ an enzyme so that cryptogamia which is killed is decomposed into products which do not putrefy and do not leave significant visible remains in the waterway.

Other objects and advantages of this invention will become apparent from a study of the following portion of the specification, the claims and the attached drawings.

DESCRIPTION OF THE PREFERRED EMBODIMENT

Figure 1:
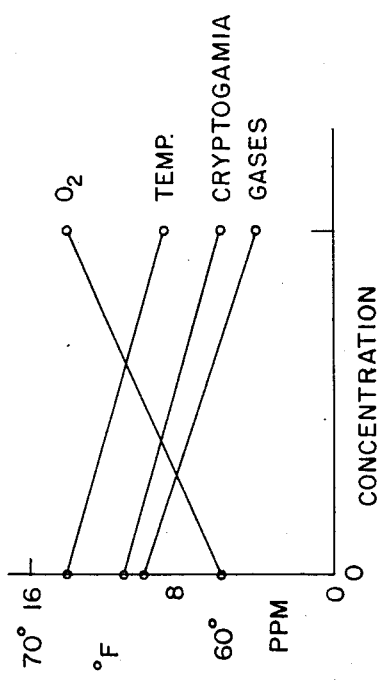
FIG. 1 is a graph showing the transmissivity versus wavelength of water which compares water with and without the waterways treatment composition of this invention in proper concentration.

This invention is directed to the concept that the enhancement of ultraviolet solar radiation into a body of water causes death to cryptogamia in the water. The dye is selected to transmit ultraviolet in wavelength from 4,000 Angstroms to below 3,000 Angstroms. While the dye need not have an effect on the visible and infrared spectrum, most violet dyes reflect a substantial portion of the radiation at wavelengths longer than 4,000 Angstroms, see FIG. 1. The preferred violet dye is C.I. Acid Violet 49, which is identified in detail in the color index of the American Association of Textile Chemists and Colorists. This dye is identified as Dye No. C.I. 42640 in that index. This dye belongs to the triphenol methane group. A concentrate solution is made by mixing 0.2 pound of that dye in a gallon of water. When the concentrate is diluted in proper proportion in a waterway, in the presence of sunlight, it causes death to the cryptogamia by permitting access of the ultraviolet to the cryptogamia. In the normal course of affairs, the dead cryptogamia falls to the bottom of the waterway with the undesirable appearance of brown mud. In order to dispose of this potential mud, at least one enzyme is provided in the concentrate solution. To achieve this, 0.1 pound of Cellubac is placed in solution in each gallon of concentrate. Cellubac is the tradename of a mixture of cellulose, protein and starch enzymes sold by Nova Laboratories. Other such enzyme mixtures are commercially available.

When the concentrate is mixed into the water in the waterway in proper concentration, after the death of the cryptogamia by ultraviolet exposure, the enzyme digests the cryptogamia into decomposition products. These decomposition products are gaseous, which dissolve into or bubble out of the water, are water-soluble so they dissolve in the water, and/or are water-insoluble so they fall to the bottom. The insoluble solid is a small fraction of the original and deposits as ash on the bottom of the waterway. Its quantity is not sufficient to be objectionable. The proper dilution ratio of the concentrate into the waterway is about 1 gallon of concentrate to 50,000 gallons of water. The acid violet dye No. 49, in the dilute solution in the waterway and in the presence of sunlight, breaks down in due course, depending upon ambient conditions. In ordinary 70 degree F. average weather, without the addition of rain water, and in normal sunlight, the acid violet dye breaks down in about two weeks. In the presence of toxins, this dye breaks down more quickly in the process of neutralizing the toxins.

During the presence of this dye, the water has a violet appearance. This appearance is objectionable from an aesthetic viewpoint and, as a consequence, it is desirable to add a blue dye to the water to mask or hide the violet appearance of the dye which is functional in killing the cryptogamia. A blue dye selected from the triphenol methane group is used. These dyes are Acid Blues Nos. 9, 11 and 15. The most preferred dye to provide this color is C.I. Acid Blue No. 11. It must be noted that this blue dye is optional and is provided only for the purpose of masking the violet color, which is not a normal color for a waterway.

C.I. Acid Violet No. 49, C.I. No. 42640, is the preferred active dye. However, other triphenol methane dyes which have an open band pass in the 3,000 to 4,000 Angstrom range should be satisfactory. Similarly, Cellubac is the preferred enzyme, but other enzyme mixtures are also suitable. As far as the optional C.I. Acid Blue No. 11 is concerned, it is preferred because it contains a triphenol methane group, similarly to the Acid Violet No. 49. However, alternative optional blue dyes are Acid Blue No. 9 and Acid Blue 15, C.I. 42645. Each of these dyes is identified in the color index in the American Association of Textile Chemists and Colorists.

Figure 2:
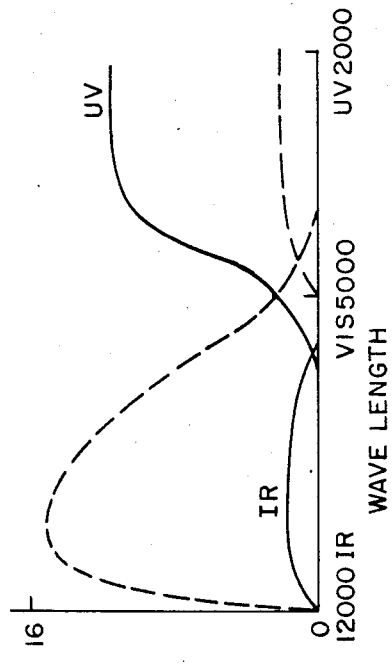
FIG. 2 is a graph which compares dissolved gases, live cryptogamia and temperature of water with and without the waterways treatment composition.
Figure 3:
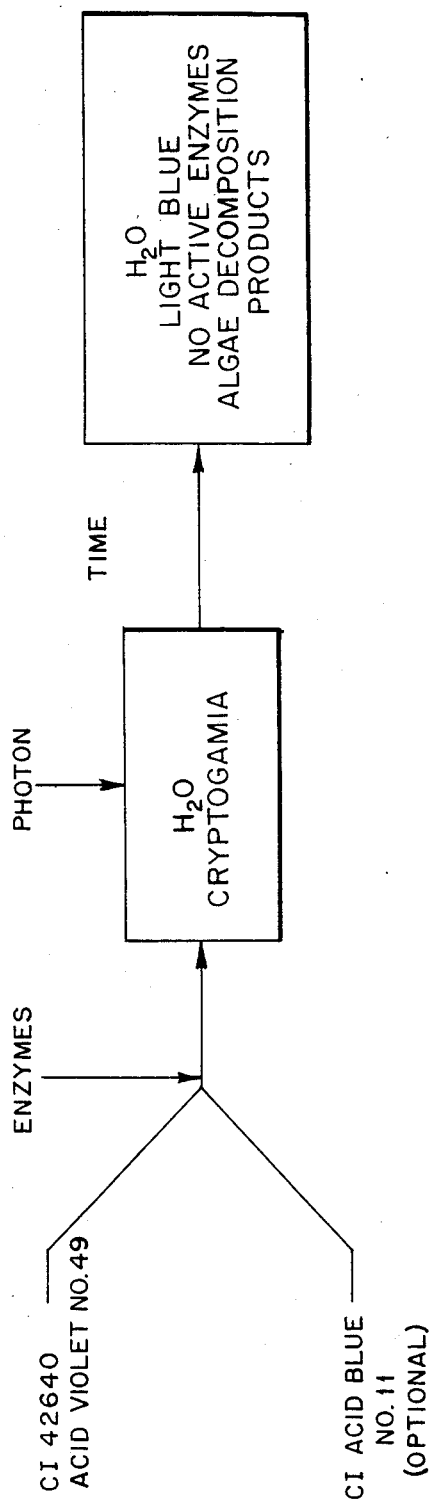
FIG. 3 is a process time diagram showing the steps which occur when the compound of this invention is added in proper concentration into a waterway.

As indicated in FIG. 3, the process comprises mixing 0.2 pound of C.I. 42640 Acid Violet No. 49 or equivalent and 0.05 pound of enzyme mixture such as Cellubac in one gallon of water. C.I. Acid Blue No. 11 is optionally added in the amount of 0.02 pound to give the waterway water a color which is pleasing to the eye. This mixed water-soluble concentrate is mixed in 50,000 gallons of water in a waterway. Exposure to normal sunlight or artificial light of at least 40 watts is a necessary part of the process. The violet dye provides greater transmissivity to ultraviolet rays from the sun than the visible or infrared. FIG. 1 shows transmissivity of both IR and UV versus wavelength of normal waterway water without (dashed lines) and with (full lines) the treatment composition. Transmissivity is measured with a standard turbidity meter with appropriate filters. Time is also a necessary part of the process. A significant amount of the cryptogamia originally present in the water in the waterway is killed during the first day of exposure to a substantial amount of ultraviolet radiation from the sun. During normal sunlight, in about two weeks the ultraviolet dye is degraded, possibly from radiation, spin, or oxidation, so that it is no longer violet in color and is no longer effective in admitting violet radiation to kill the cryptogamia. During the active period of the dye, the water temperature goes down because either the incident radiation is partially converted from the visible and infrared wavelengths into ultraviolet, or the visible and infrared are rejected from the surface of the water. This occurs whether or not the optional blue dye has been added for appearance purposes. The optional blue dye lasts longer than the violet dye, so the water maintains its blue color, if the optional dye has been added. FIG. 2 shows the effect of the compound on material in the water. It decreases live cryptogamia and undesirable gases such as $CO_2$, $H_2S$ and inert gases. It also causes a decrease in temperature and an increase in dissolved oxygen.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A composition for the treatment of waterways, said composition comprising:
   a water-soluble violet dye to permit the substantial transmission of the ultraviolet fraction of ambient solar light and to reduce the transmission into the waterway of the fraction of solar light of longer wavelength than ultraviolet so as to kill at least some of the cryptogamia in the waterway; and
   an enzyme for digesting killed cryptogamia in the waterway.

2. The waterways treatment composition of claim 1 wherein the enzyme is a mixture of protein, cellulose and starch digesting enzymes.

3. The waterways treatment composition of claim 1 wherein said violet dye is selected from the triphenol methane group consisting of Acid Violet No. 49.

4. The waterways treatment composition of claim 3 wherein the enzyme is a mixture of protein, cellulose and starch digesting enzymes.

5. The waterways treatment composition of claim 4 further including a water-soluble blue dye for masking the color of the violet dye and giving a blue appearance to the waterway, said blue dye being substantially ineffective for reducing ultraviolet transmissivity into the waterway.

6. The waterways treatment composition of claim 5 wherein said blue dye is selected from the triphenol methane group consisting of Acid Blue Nos. 9, 11 and 15.

7. The waterways treatment composition of claim 1 further including a water-soluble blue dye for masking the color of the violet dye and giving a blue appearance to the waterway, said blue dye being substantially ineffective for reducing ultraviolet transmissivity into the waterway.

8. The waterways treatment composition of claim 7 wherein said blue dye is triphenol-methane dye.

9. A concentrated waterways treatment composition comprising:
   a violet dye and an enzyme in water solution, said violet dye being selected to substantially permit the transmission of solar ultraviolet into a waterway when said composition is properly diluted in the waterway so that the transmission of ultraviolet light into the waterway causes death of cryptogramia previously living in the waterway, said ultraviolet dye being selected to limit the transmission of solar radiation having a longer wavelength than ultraviolet, said enzyme being selected to digest at least part of the killed cryptogamia.

10. The waterways treatment composition of claim 9 wherein the enzyme is a mixture of protein, cellulose and starch digesting enzymes.

11. The waterways treatment composition of claim 9 wherein said violet dye is selected from the triphenol methane group consisting of Acid Violet No. 49.

12. The waterways treatment composition of claim 11 wherein the enzyme is a mixture of protein, cellulose and starch digesting enzymes.

13. The waterways treatment composition of claim 12 further including a water-soluble blue dye for masking the color of the violet dye and giving a blue appearance to the waterway, said blue dye being substantially ineffective for reducing ultraviolet transmissivity into the waterway.

14. The waterways treatment composition of claim 13 wherein said blue dye is selected from the triphenol methane group consisting of Acid Blue Nos. 9, 11 and 15.

15. The waterways treatment composition of claim 9 further including a water-soluble blue dye for masking the color of the violet dye and giving a blue appearance to the waterway, said blue dye being substantially ineffective for reducing ultraviolet transmissivity into the waterway.

16. The waterways treatment composition of claim 15 wherein said blue dye is a triphenol methane dye.

17. The concentrate composition of claim 9 wherein there is sufficient violet dye that when said concentrate is diluted in a waterway, there is about 0.2 pound of violet dye per 50,000 gallons of water in the waterway.

18. The concentrate composition of claim 9 wherein there is sufficient enzyme in said said concentrate so that when diluted into a waterway, there is about 0.05 pound of enzyme in each 50,000 gallons of water in the waterway.

19. The concentrate composition of claim 12 wherein there is sufficient blue dye in said said concentrate that when said concentrate is diluted into a waterway, there is about 0.2 pound of blue dye per 50,000 gallons of water in the waterway.

20. The method of treating a waterway to limit the growth of cryptogamia therein, comprising the steps of:
  mixing a water-soluble violet dye into the waterway so as to permit the transmission of solar ultraviolet radiation into the waterway and limit transmission of longer wave solar radiation into the waterway to kill cryptogamia in the waterway; and
  introducing an enzyme into the waterway to digest killed cryptogamia in the waterway.

21. The method of claim 20 wherein the violet dye is Acid Violet No. 49.

22. The method of claim 21 wherein the enzyme is a mixture of protein, starch and cellulose digesting enzymes.

23. The method of claim 20 wherein the enzyme is a mixture of protein, starch and cellulose digesting enzymes.

24. The method of claim 20 further including the step of mixing into the waterway a water-soluble blue dye in sufficient quantity to substantially hide the violet color of the violet dye.

25. The method of claim 24 wherein the blue dye is a triphenol methane dye and the blue dye is provided in sufficient quantity so that there is about 0.2 pound per 50,000 gallons of water in the waterway.

* * * * *